United States Patent [19]

Callaghan

[11] Patent Number: 4,579,119
[45] Date of Patent: Apr. 1, 1986

[54] METHOD AND APPARATUS FOR MULTIPLEXED DIPOLE/QUADRUPOLE FOR STIMULATION/SENSING

[75] Inventor: Frank J. Callaghan, Miami, Fla.

[73] Assignee: Cordis Corporation, Miami, Fla.

[21] Appl. No.: 553,260

[22] Filed: Nov. 18, 1983

[51] Int. Cl.⁴ .............................................. A61N 1/36
[52] U.S. Cl. ............................................. 128/419 PG
[58] Field of Search ........... 128/784, 785, 786, 419 D, 128/419 P, 419 PG, 642

[56] References Cited

U.S. PATENT DOCUMENTS

| | | | |
|---|---|---|---|
| 3,995,623 | 12/1976 | Blake et al. | 128/419 P |
| 4,088,140 | 5/1978 | Rockland et al. | 128/419 PG |
| 4,289,134 | 9/1981 | Bernstein | 128/419 PG |
| 4,365,639 | 12/1982 | Goldreyer | 128/419 PG |
| 4,444,195 | 4/1984 | Gold | 128/642 |

FOREIGN PATENT DOCUMENTS 30897 12/1980 European Pat. Off. ..... 128/419 PG

Primary Examiner—William E. Kamm
Attorney, Agent, or Firm—George H. Gerstman

[57] ABSTRACT

A system is provided for cardiac pacing and sensing. A lead carrying three electrodes is introduced into a cardiac chamber. Two of the electrodes are connected to the output of a pulse generator and are disconnected from the pulse generator output during sensing. All three of the electrodes are connected to the input of a sensing amplifier during sensing and two of the electrodes are disconnected from the input during pacing.

10 Claims, 1 Drawing Figure

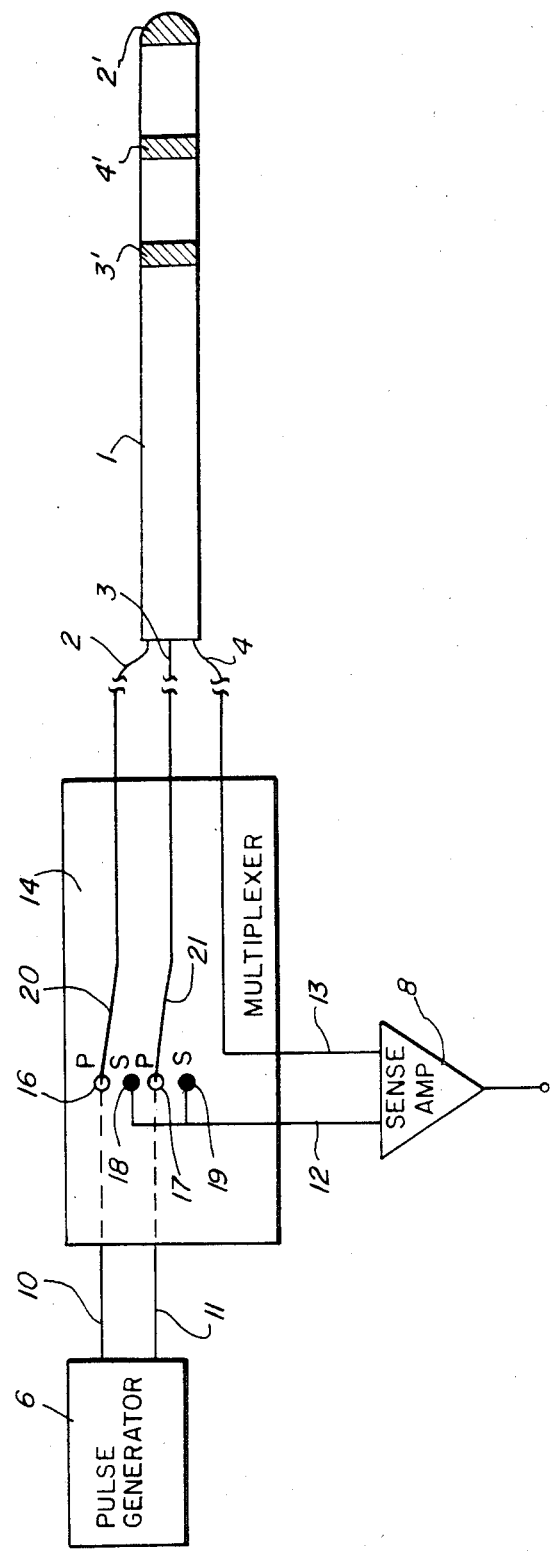

METHOD AND APPARATUS FOR MULTIPLEXED DIPOLE/QUADRUPOLE FOR STIMULATION/SENSING

BACKGROUND OF THE INVENTION

The present invention concerns a novel system for cardiac pacing and sensing.

In both unipolar and bipolar cardiac pacing, in which a lead is located in a cardiac chamber, after a current pulse is applied polarization charges exist in solution at the electrode-electrolyte interface. These charges are electrolytic ions which are intrinsic to the volume conductor. Anions are found surrounding the anode while cations are established at the cathode. As a result, during sensing it is often difficult to sense the evoked cardiac response because the polarization voltages may be greater than the cardiac signals. In effect, the sensing circuit of the pacer is unable to determine whether the pulse provided by the pacer has been an effective stimulus because the pulse that was provided results in a polarization charge that masks the cardiac response. It has been determined to be the pacer's sensing circuit that is effectively unable to determine the response.

The use of a three-electrode configuration in the atrium for the purpose of reducing cross-sensing (i.e., cross-talk) from the ventricle during sensing has been suggested prior to this invention. I have discovered that by using three electrodes in either of the cardiac chambers, all three electrodes may be used for sensing and two of the same three electrodes may be used for pacing with the result that in addition to alleviating the cross-talk problem as previously noted, the polarization problem is also alleviated. I have found that by using the three electrodes, the polarization potential as seen by the electrodes is reduced sufficiently so that the electrodes readily can "read" the cardiac evoked response.

Other objects and advantages of the present invention will become apparent as the description proceeds.

SUMMARY OF THE INVENTION

In accordance with the present invention, a system is provided for cardiac pacing and sensing including means for generating pacing pulses and means for sensing cardiac response. The improvement comprises a lead for introduction into a cardiac chamber, with the lead carrying three electrodes. Switching means are coupled to the pulse generating means and the sensing means, with the switching means being operable to connect two of the electrodes to the pulse generating means during pacing and being operable to connect all three of the electrodes to the sensing means during sensing.

In the illustrative embodiment, the switching means are operable to disconnect the sensing means from at least two of the electrodes during pacing and to disconnect the pulse generating means from the electrodes during sensing.

In the illustrative embodiment, the pulse generating means include two output lines and the sensing means include two input lines. The switching means operate to connect two of the electrodes to the two output lines during pacing and to connect the same two of the electrodes to one of the input lines during sensing. The other of the three electrodes is connected to the other of the input lines during both pacing and sensing.

In the illustrative embodiment, the electrodes are in the form of a distal tip electrode and two spaced ring electrodes, with wires extending from the tip and rings to the switching means. The wires are carried internally within a lead cover.

A more detailed explanation of the invention is provided in the following description and claims, and is illustrated in the accompanying drawing.

BRIEF DESCRIPTION OF THE DRAWING

The drawing is a schematic diagram of a system for cardiac pacing and sensing constructed in accordance with the principles of the present invention.

DETAILED DESCRIPTION OF THE ILLUSTRATIVE EMBODIMENT

Referring to the drawing, a cardiac lead 1 is schematically illustrated therein. Cardiac lead 1 is adapted for introduction into one of the cardiac chambers. Conventionally, lead 1 will be a straight lead if used in the ventricle and will have a J-shape if used in the atrium.

Lead 1 comprises a plastic lead cover carrying three wires 2, 3 and 4, internally. Wire 2 is electrically connected to a distal tip electrode 2'; wire 3 is electrically connected to a spaced ring electrode 3'; and wire 4 is electrically connected to another spaced ring electrode 4'. The use of tip and ring electrodes on plastic leads in cardiac pacing and sensing is well-known in the art.

Conventionally, cardiac pacers comprise a pulse generator 6 for generating pacing pulses and a sensing amplifier 8 for sensing cardiac response. In accordance with the present invention, pulse generator 6 has output lines 10 and 11 for providing the basic pulses and sense amplifier 8 has input lines 12 and 13 for detecting the cardiac response. A multiplexer 14 is provided for connecting and disconnecting the electrodes to the pulse generator 6 and sense amplifier 8 in a novel manner. In its schematic form, multiplexer 14 has switch contacts 16 and 17 which are connected, respectively, to output lines 10 and 11 of pulse generator 6. Multiplexer 14 also has switch contacts 18 and 19 which are both connected to sense amplifier input line 12. Wire 2 is connected to switch arm 20 and wire 3 is connected to switch arm 21.

During pacing, switch arms 20 and 21 engage contacts 16 and 17, respectively, as illustrated. In this manner, electrodes 2' and 3' are coupled to outputs 10 and 11, respectively, of the pulse generator 6 and are effectively disconnected from the sense amplifier 8. However, electrode 4' is always connected to input 13 of sense amplifier 8.

During sensing, switch arms 20 and 21 will engage contacts 18 and 19. In this manner, electrodes 2' and 3' will be connected to input 12 of sense amplifier 8 and will be effectively disconnected from pulse generator 6.

Since the cardiac response detection is differential, it does not matter which input of sense amplifier 8 is used for connection to electrode 4' so long as electrode 4' is connected to a different input from electrodes 2' and 3'.

Although a multiplexer 14 is illustrated with discrete switches, this is by example only and the multiplexer may take the form of a unit containing discrete solid state devices, discrete mechanical devices or it may be the form of a software routine utilizing a microprocessor-based system.

By using three electrodes for sensing and two of the same three electrodes for pacing, both the problem of cross-talk between chambers and the problem of polarization is alleviated.

Although an illustrative embodiment of the invention has been shown and described, it is to be understood that modifications and substitutions may be made by those skilled in the art without departing from the novel spirit and scope of the present invention.

What is claimed is:

1. In a system for cardiac pacing including means for generating pacing pulses and means for sensing cardiac response, the improvement comprising:
    a lead for introduction into only one cardiac chamber, said lead including means for pacing and sensing within one chamber, said means including three electrodes for location within said one chamber;
    switching means coupled to said pulse generating means and said sensing means;
    said switching means for connecting two of said electrodes to said pulse generating means during pacing and being operable to connect all three of said electrodes to said sensing means during sensing whereby the polarization as seen by the electrodes is reduced sufficiently so that the electrodes can read the cardiac evoked response.

2. In the system as described in claim 1, said switching means being operable to disconnect said sensing means from at least two of said electrodes during pacing and to disconnect said pulse generating means from said electrodes during sensing.

3. In a system as described in claim 1, said electrodes being in the form of a distal tip electrode and two spaced ring electrodes, with wires extending from said tip and rings to said switching means, said wires being carried internally within a lead cover.

4. In a system as described in claim 1, said pulse generating means including two output lines and said sensing means including two input lines; said switching means being operable to connect two of said electrodes to said two output lines during pacing and to connect the same two of said electrodes to one of said input lines during sensing.

5. In a system as described in claim 4, wherein the other of said three electrodes is connected to the other of said input lines during pacing and sensing.

6. In a system as described in claim 1, said pulse generating means including a first output line and a second output line; said sensing means including a first input line and a second input line; said three electrodes including a first electrode for connection by said switching means to said first output line during pacing and for connection to said first input line during sensing, a second electrode for connection by said switching means to said second output line during pacing and for connection to said first input line during sensing; and a third electrode for connection by said switching means to said second input line during pacing and sensing.

7. In a system as described in claim 6, said electrodes being in the form of a distal tip electrode and two spaced ring electrodes, with wires extending from said tip and rings to said switching means, said wires being carried internally within a lead cover.

8. A cardiac pacing process in which a pulse generator provides pacing pulses and means are provided for sensing cardiac response, including the steps of:
    introducing into only one cardiac chamber a lead including means for pacing and sensing within one chamber, said means including three electrodes for location within one chamber;
    connecting two of said electrodes to said pulse generator during pacing;
    disconnecting said two electrodes from said pulse generator during sensing;
    connecting all three electrodes to said sensing means during sensing whereby the polarization potential as seen by the electrodes is reduced sufficiently so that the electrodes can read the cardiac evoked response; and
    disconnecting at least two of said electrodes from said sensing means during pacing.

9. A cardiac pacing process as described in claim 8, wherein said one of three electrodes is connected to said sensing means during pacing and sensing.

10. A cardiac pacing process as described in claim 8, including the step of providing one of the electrodes at the distal tip of the lead and providing the other two electrodes as spaced rings on the lead.

* * * * *